(12) United States Patent
Cern

(10) Patent No.: US 11,493,943 B2
(45) Date of Patent: Nov. 8, 2022

(54) SYSTEMS, DEVICES, AND METHODS FOR PROVIDING A REGULATED CURRENT TO A VARYING RESISTIVE LOAD

(71) Applicant: Healables, Ltd., Jerusalem (IL)

(72) Inventor: Yehuda Cern, Efrat (IL)

(73) Assignee: HEALABLES, LTD., Jerusalem (IL)

( * ) Notice: Subject to any disclaimer, the term of this patent is extended or adjusted under 35 U.S.C. 154(b) by 0 days.

(21) Appl. No.: 17/154,484

(22) Filed: Jan. 21, 2021

(65) Prior Publication Data

US 2021/0141406 A1 May 13, 2021

Related U.S. Application Data

(63) Continuation-in-part of application No. PCT/IL2019/050733, filed on Jul. 2, 2019.

(60) Provisional application No. 62/703,256, filed on Jul. 25, 2018, provisional application No. 62/703,244, filed on Jul. 25, 2018.

(51) Int. Cl.
*G05F 1/46* (2006.01)
*G05F 1/56* (2006.01)
*G05F 1/565* (2006.01)
*H02M 3/156* (2006.01)
*H02M 1/00* (2006.01)
*G05F 1/575* (2006.01)

(52) U.S. Cl.
CPC ............. *G05F 1/46* (2013.01); *G05F 1/562* (2013.01); *G05F 1/565* (2013.01); *G05F 1/575* (2013.01); *H02M 1/009* (2021.05); *H02M 3/156* (2013.01)

(58) Field of Classification Search
CPC . G05F 1/46; G05F 1/562; G05F 1/565; G05F 1/575; H02M 1/009; H02M 3/156
See application file for complete search history.

(56) References Cited

U.S. PATENT DOCUMENTS

| 6,377,853 B1 | 4/2002 | Malaney et al. |
| 8,760,141 B2 * | 6/2014 | Man ..................... H02M 3/156 323/284 |

(Continued)

FOREIGN PATENT DOCUMENTS

| EP | 0 847 293 A1 | 6/1998 |
| WO | 2014165111 | 10/2014 |

*Primary Examiner* — Kyle J Moody
*Assistant Examiner* — Lakaisha Jackson
(74) *Attorney, Agent, or Firm* — Browdy and Neimark, PLLC

(57) ABSTRACT

A voltage booster powered by a primary electrical source for providing an adjustable voltage across the load, while a current regulator in series with the load maintains the desired current. When the voltage drop across the current regulator exceeds an upper threshold, the voltage booster's output voltage is reduced to a lower level to reduce the power dissipated by the current regulator, to improve efficiency. When the voltage drop across the current regulator is less than a lower threshold, the voltage booster output is increased to a higher level. In burst mode operation, the voltage booster output alternates between a full voltage and zero voltage, and an optional capacitor provides voltage across the resistive load during discharge. An optional diode can ensure that the capacitor discharges through the load in cases where the voltage booster output is not floating.

16 Claims, 4 Drawing Sheets

(56) References Cited

U.S. PATENT DOCUMENTS

| | | | |
|---|---|---|---|
| 2006/0221528 A1* | 10/2006 | Li | H02M 1/32 |
| | | | 361/100 |
| 2008/0084117 A1* | 4/2008 | Sander | H02J 3/385 |
| | | | 307/46 |
| 2010/0114257 A1 | 5/2010 | Torgerson | |
| 2012/0081016 A1 | 4/2012 | Wu et al. | |
| 2013/0342124 A1 | 12/2013 | Huang et al. | |
| 2014/0009134 A1* | 1/2014 | Bernardon | H02M 3/156 |
| | | | 323/284 |
| 2014/0214111 A1 | 7/2014 | Greiner et al. | |
| 2014/0292220 A1 | 10/2014 | Trattler | |
| 2015/0066108 A1 | 3/2015 | Shi et al. | |
| 2016/0126838 A1 | 5/2016 | Cavallini et al. | |
| 2016/0367813 A1 | 12/2016 | Pepin et al. | |

\* cited by examiner

SYSTEMS, DEVICES, AND METHODS FOR PROVIDING A REGULATED CURRENT TO A VARYING RESISTIVE LOAD

CROSS-REFERENCE TO RELATED APPLICATIONS

This application is a continuation-in-part (CIP) application of PCT Application No. PCT/IL2019/050733 entitled "Regulated Current Power Source" filed Jul. 2, 2019, which claims the benefit of i) U.S. Provisional Patent Application No. 62/703,256 entitled "Burst mode constant-current power supply system", and ii) U.S. Provisional Patent Application No. 62/703,244, entitled "Constant-current power supply system", both filed on Jul. 25, 2018, the subject matter of all three of these patent applications being herein incorporated by reference in their entireties.

FIELD

Disclosed aspects relate to electrical power devices and systems based on regulated current sources.

BACKGROUND

Electric power sources, such as batteries and mains outlets, typically provide a regulated voltage that can be applied directly to power a load in certain cases. In contrast, a regulated current is often needed for biological and similar loads that typically have a widely-varying resistance.

FIG. 1 is a block diagram of a simple conventional configuration for a regulated current source 100. A primary electrical energy source 105 supplies a voltage $V_{in}$ 106, measured relative to a local (chassis) ground 107, which is connected to an input 111 of a voltage booster 110 to provide a higher voltage $V_{out}$ 108 at a power-out point 112. $V_{out}$ 108 is connected to an output terminal 135, which is connected to one lead of an external load 150 having a varying resistance $R_{var}$. Another output terminal 130 of regulated current source 100 is connected to the other lead of external load 150. It is desired to drive a regulated current hoax 140 through external load 150. Thus, output terminal 130 is connected to a current regulator 120 which is adjusted to pass regulated current $I_{load}$ 140, by automatically changing its internal resistance. As a result, a varying regulator voltage drop $V_{reg}$ 145 appears across current regulator 120, which varies with changes in the value of $R_{var}$.

A configuration such as regulated current source 100 is highly inefficient because current regulator 120 dissipates power P=Vreg*Iload, which is wasted, as it is not utilized by external load 150.

Known mains constant-current power supplies integrate a current regulator in which feedback is used to actuate mechanisms such as pulse width modulation (PWM). Several arrangements are based on this technology, but none provide separate voltage boosters (and/or regulators) with separate current regulators.

SUMMARY

Disclosed aspects recognize it is desirable to have a more efficient regulated current source utilizing a boosted voltage, which still retains the simplicity and reliability of the regulated current source 100 described above in the background. This goal is achieved by disclosed aspects.

Disclosed aspects include a regulated current source device electrically coupled with a controlled voltage booster and a controller therefor. The controller senses change in load resistance, and in response thereto adjusts an operational parameter of the voltage booster to result in improved efficiency with reduced power dissipation.

Therefore, according to a disclosed aspect, a regulated current source device is for providing a regulated current to a resistive load, the regulated current source device including: (a) a primary electrical energy source providing an input voltage; (b) a voltage booster which receives the input voltage and provides an adjustable voltage from a power-out point, wherein the adjustable voltage is controllable via a control signal at a control point of the voltage booster; (c) a current regulator, which regulates a current through the resistive load according to a predetermined regulated load current; and (d) a controller for measuring a voltage drop across the current regulator, and for controlling the voltage booster via the control point according to the voltage drop.

In addition, according to another disclosed aspect there is disclosed a method for providing a regulated current to a resistive load, the method comprising: (a) initializing a current regulator to pass a predetermined load current through the resistive load; (b) initializing a voltage booster to output an initial output voltage to the resistive load, wherein the voltage booster receives an input voltage from a primary electrical energy source, wherein the voltage booster output voltage is controllable according to a control signal, and wherein the initializing comprises sending a first control signal to the voltage booster; (c) measuring a voltage drop across the current regulator to obtain a current regulator voltage drop measure; (d) comparing the current regulator voltage drop measure to a predetermined upper threshold; and (e) when the current regulator voltage drop measure is greater than the upper threshold, then sending a second control signal to the voltage booster to output a reduced output voltage to the resistive load, wherein the reduced output voltage equals the output voltage minus an incremental output voltage change value; (f) comparing the current regulator voltage drop measure to a predetermined lower threshold; and (g) when the current regulator voltage drop measure is less than the lower threshold, then sending a third control signal to the voltage booster to output an increased output voltage, wherein the increased output voltage equals the output voltage plus the incremental output voltage change value.

BRIEF DESCRIPTION OF THE DRAWINGS

The subject matter disclosed herein may best be understood by reference to the following detailed description when read with the accompanying drawings in which:

FIG. 2b is a block diagram of a regulated current source device according to a disclosed aspect related to the regulated current source of FIG. 2a.

Figure 1:
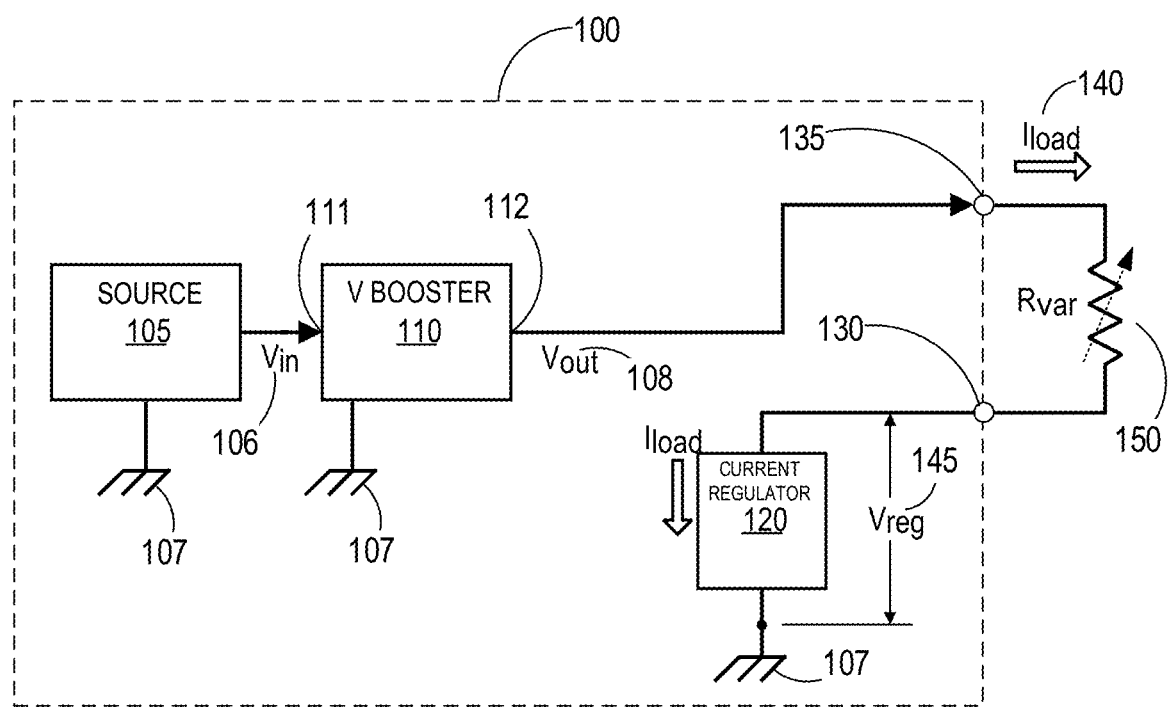
FIG. 1 is a block diagram of a conventional configuration for a regulated current source.

For simplicity and clarity of illustration, elements shown in the figures are not necessarily drawn to scale, and the dimensions of some elements may be exaggerated relative to other elements. In addition, reference numerals may be repeated among the figures to indicate corresponding or analogous elements.

DETAILED DESCRIPTION

Figure 2A:
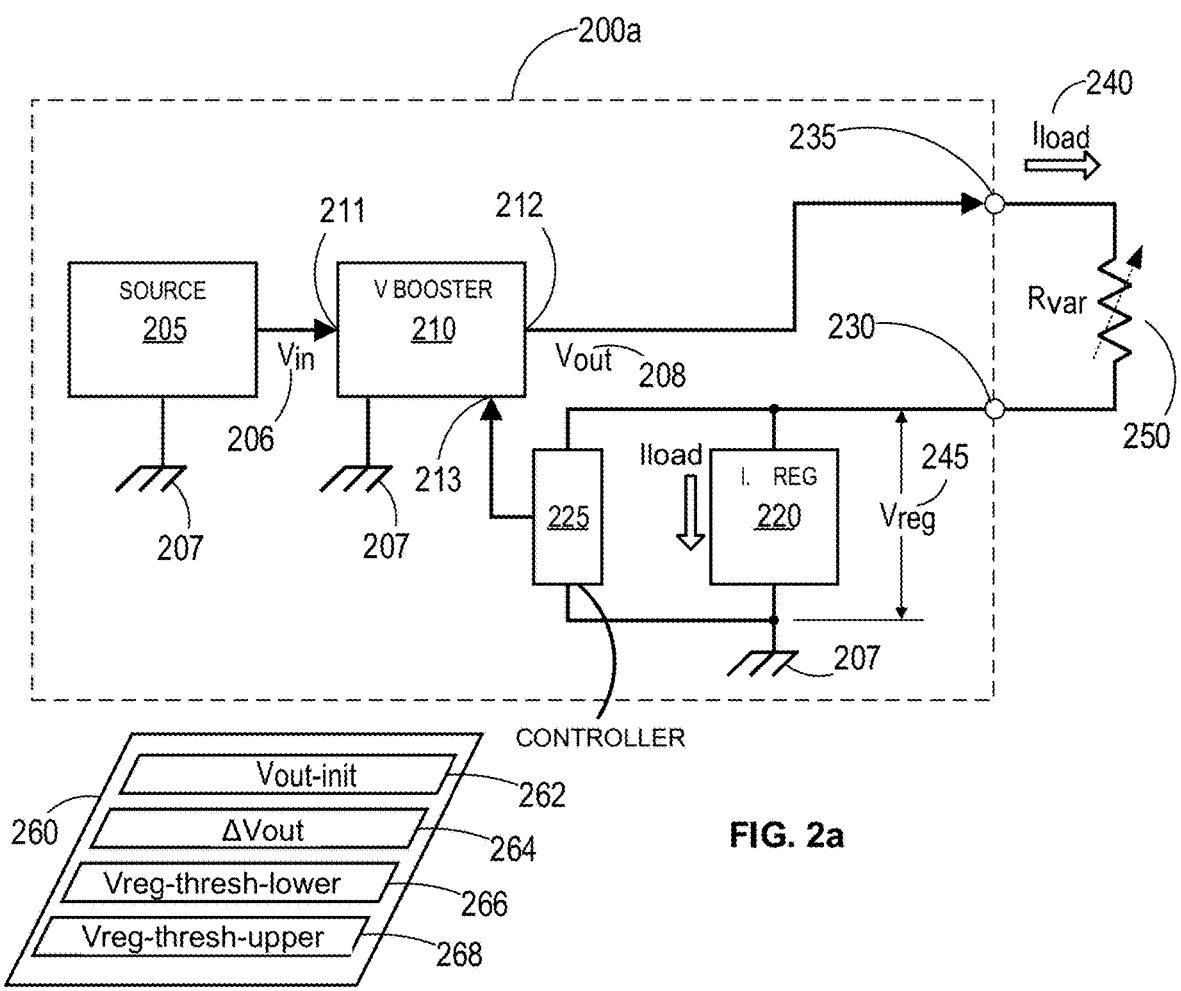
FIG. 2a is a block diagram of a regulated current source device according to a disclosed aspect.

FIG. 2a is a block diagram of a regulated current source device 200a according to a disclosed aspect. A primary electrical energy source 205 supplies an input voltage $V_{in}$ 206, measured relative to a local (chassis) ground 207, which is connected to an input 211 of a voltage booster 210 to provide an adjustable voltage $V_{out}$ 208 at a power-out point 212. In particular, voltage $V_{out}$ 208 may be greater than voltage $V_{in}$. $V_{out}$ 208 is connected to an output terminal 235, which is connected to one lead of an external resistive load 250 having a varying resistance $R_{var}$. Another output terminal 230 of regulated current source device 200a is connected to the other lead of external load 250. It is desired to drive a regulated load current ($I_{load}$) 240 through external load 250. Thus, output terminal 230 is connected to a current regulator 220 which is adjusted to pass a predetermined regulated load current $I_{load}$ 240, by automatically changing its internal resistance. As a result, a varying regulator voltage drop $V_{reg}$ 245 appears across current regulator 220, which varies with changes in the value of $R_{var}$.

According to this disclosed aspect, a controller 225 senses $V_{reg}$ 245, and outputs a control signal to a control point 213 of voltage booster 210 according to which, voltage booster 210 adjusts output voltage $V_{out}$ 208.

Controller 225 adjusts output voltage $V_{out}$ 208 according to a parameter set 260, which includes:
  an initial output voltage value $V_{out-init}$ 262;
  an incremental change in output voltage value $\Delta V_{out}$ 264;
  a first regulator voltage drop threshold $V_{reg-thresh-lower}$ 266; and
  a second regulator voltage drop threshold $V_{reg-thresh-upper}$ 268, such that:

$$V_{reg-thresh-lower} < V_{reg-thresh-upper}.$$

Controller 225 performs the adjustment of output voltage $V_{out}$ 208 utilizing parameter set 260 according to procedures as disclosed in the discussion below relating to the method shown in FIG. 3.

In summary, a related disclosed aspect provides control as follows: voltage booster 210 supplies voltage $V_{out}$ 208, which is initially set by controller 225 (via control point 213) to $V_{out-init}$ 262, for driving the desired current $I_{load}$ 240 through external load $R_{var}$ 250. The current through external load $R_{var}$ 250 is limited to Load 240 by current regulator 220. Controller 225 continually monitors voltage drop $V_{reg}$ 245, and if $V_{reg}$ 245 exceeds threshold $V_{reg-thresh-upper}$ 268, this is taken as an indication that excessive power is being dissipated by current regulator 220, and that regulated current source device 200a is operating inefficiently. In response, controller 225 signals voltage booster 210 to output a reduced voltage $V_{out}-\Delta V_{out}$, which in turn results in a reduction in voltage drop $V_{reg}$ 245, and hence a reduction in dissipated power. The sensing of $V_{reg}$ 245 is continually repeated, and if $V_{reg}$ 245 still exceeds threshold $V_{reg-thresh-upper}$ 268, the reduction of $V_{out}$ to $V_{out}-\Delta V_{out}$ is repeated until $V_{reg}$ 245 no longer exceeds threshold $V_{reg-thresh-upper}$ 268.

Should external load resistance $R_{var}$ 250 increase, for example, resulting in a reduction of voltage drop $V_{reg}$ 245 to a value below threshold $V_{reg-thresh-lower}$ 266, controller 225 signals voltage booster 210 (again, via control point 213) to output an increased voltage $V_{out}+\Delta V$. As the sensing of $V_{reg}$ 245 proceeds, if $V_{reg}$ 245 is still below threshold $V_{reg-thresh-lower}$ 266, the increase of $V_{out}$ to $V_{out}+\Delta V_{out}$ is repeated until $V_{reg}$ 245 is no longer below threshold $V_{reg-thresh-lower}$ 266. If $V_{reg}$ 245 is neither below $V_{reg-thresh-lower}$ 266 nor above $V_{reg-thresh-upper}$ 268, then no change is made to $V_{out}$.

It is understood that the above-described disclosed aspect and its description are illustrative and non-limiting, and that other arrangements derivable from what is disclosed herein include additional voltage control schemes.

Figure 2B:
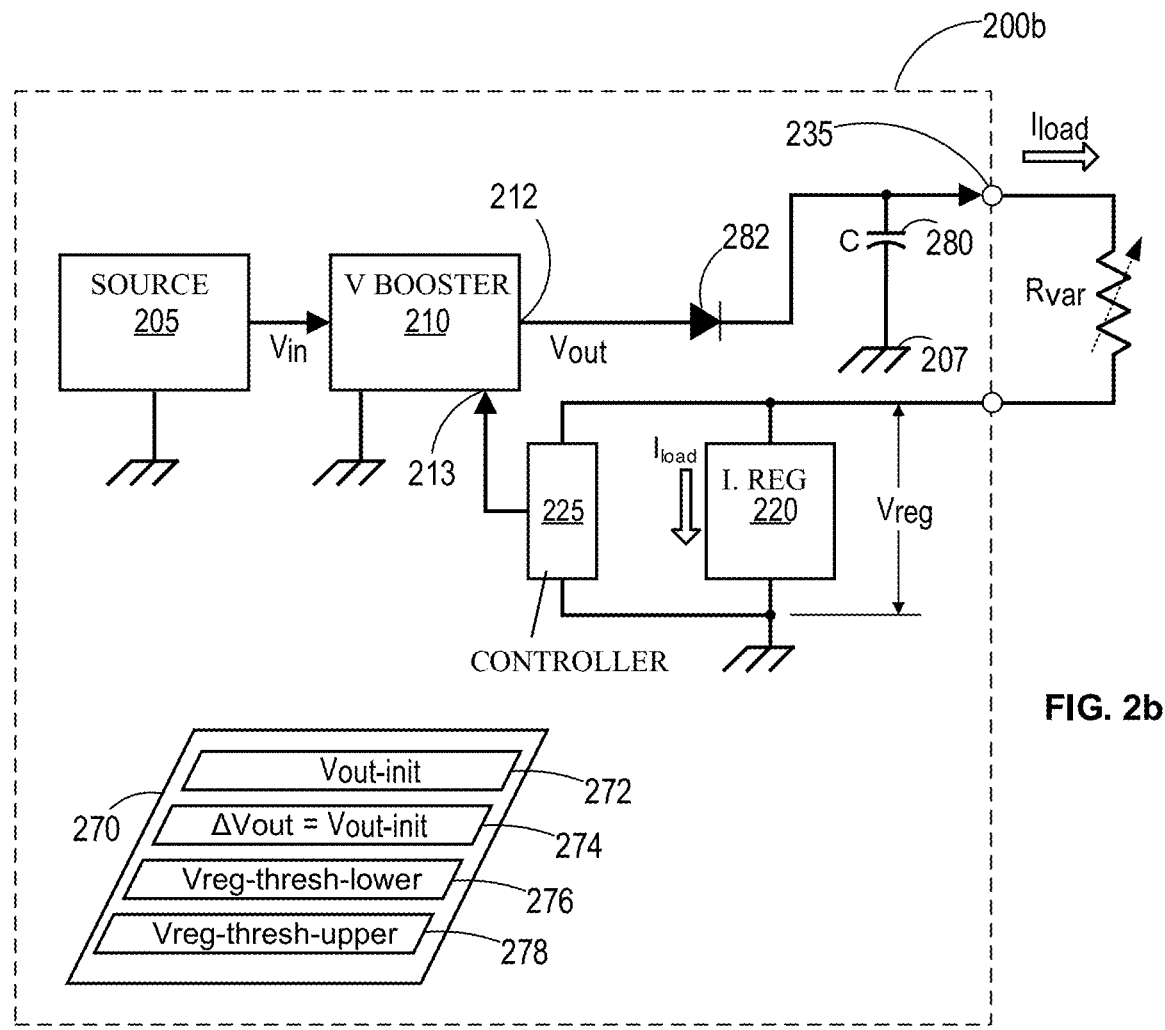

FIG. 2b is a block diagram of a regulated current source device 200b according to a disclosed aspect. As with regulated current source device 200a shown in FIG. 2a, regulated current source device 200b includes a primary electrical energy source 205 that supplies an input voltage $V_{in}$ 206 measured relative to a local (chassis) ground 207, which is connected to an input 211 of a voltage booster 210 to provide an adjustable voltage $V_{out}$ 208 at a power-out point 212. A functional feature of this related aspect is that it employs a parameter set 270 having a $V_{out-init}$ 272; a $V_{reg-thresh-lower}$ 276; and a $V_{reg-thresh-upper}$ 278, corresponding respectively to the values of parameter set 260 in FIG. 2a. However, in this related aspect for regulated current source device 200b, $\Delta V_{out}$ 274 is set to $V_{out-init}$, so that when reducing the output voltage from its initial value, the output voltage will be reduced to 0 volts ($V_{init} - \Delta V_{out} = 0$); and when increasing the output voltage from 0 volts, the output voltage will be restored to its initial value ($0 + \Delta V_{out} = V_{out-init}$). That is, regulated current source device 200b operates in "burst mode", wherein voltage is supplied by voltage booster 210 to the external load intermittently.

In order for there to be continuity of current through external load Rvar, a capacitor C 280 between output terminal 235 and local ground 207 stores charge when voltage booster 210 outputs Vout-init 272 and discharges when voltage booster 210 outputs 0 volts (Vout-init-$\Delta V$). An optional diode 282 ensures that capacitor C 280 discharges through external load Rvar when voltage booster 210 outputs zero volts. Diode 282 is not needed in cases where voltage booster 210 features a floating power-out point 212. Moreover, capacitor C 280 is optional and not needed in cases where voltage booster 210 features a floating capacitively-stabilized power-out point.

The configuration of FIG. 2b provides an improvement in efficiency by virtue of the fact that the voltage supplied by capacitor C 280 during discharge is inherently reduced and less than Vout-init 272 and thus results in reduced power dissipation.

Figure 2C:
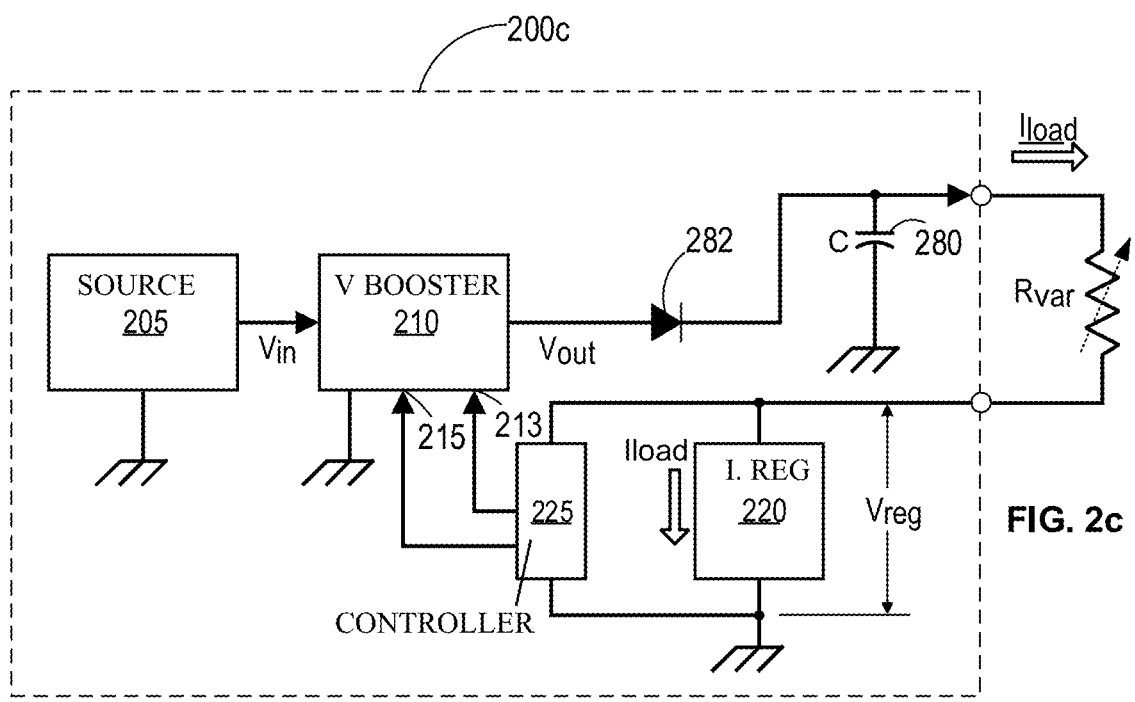
FIG. 2c is a block diagram of a regulated current source device according to another disclosed aspect related to the regulated current source of FIG. 2b.

FIG. 2c is a block diagram of a regulated current source device 200c according to another related aspect. As with regulated current source device 200a shown in FIG. 2a and regulated current source device 200b shown in FIG. 2b, the regulated current source device 200c includes a primary electrical energy source 205 that supplies an input voltage $V_{in}$ 206 measured relative to a local (chassis) ground 207, which is connected to an input 211 of a voltage booster 210 to provide an adjustable voltage $V_{out}$ 208 at a power-out point 212. Regulated current source device 200c also operates in "burst mode" as does regulated current source device 200b (FIG. 2b), but rather than utilizing a modified parameter set (as parameter set 270 of FIG. 2b), regulated current source device 200c operates in "burst mode" via a shutdown point 215 of voltage booster 210. Shutdown point 215 is separate and distinct from control point 213. During the time a shutdown signal is applied to shutdown point 215, voltage booster 210 ceases operation and provides zero volts at power-out point 212. When the shutdown signal is removed, voltage booster 210 resumes providing voltage at power-out point 212 according to the signal at control point 213. The above comments regarding capacitor C 280 and diode 282 also apply to regulated current source device 200c.

Figure 3:
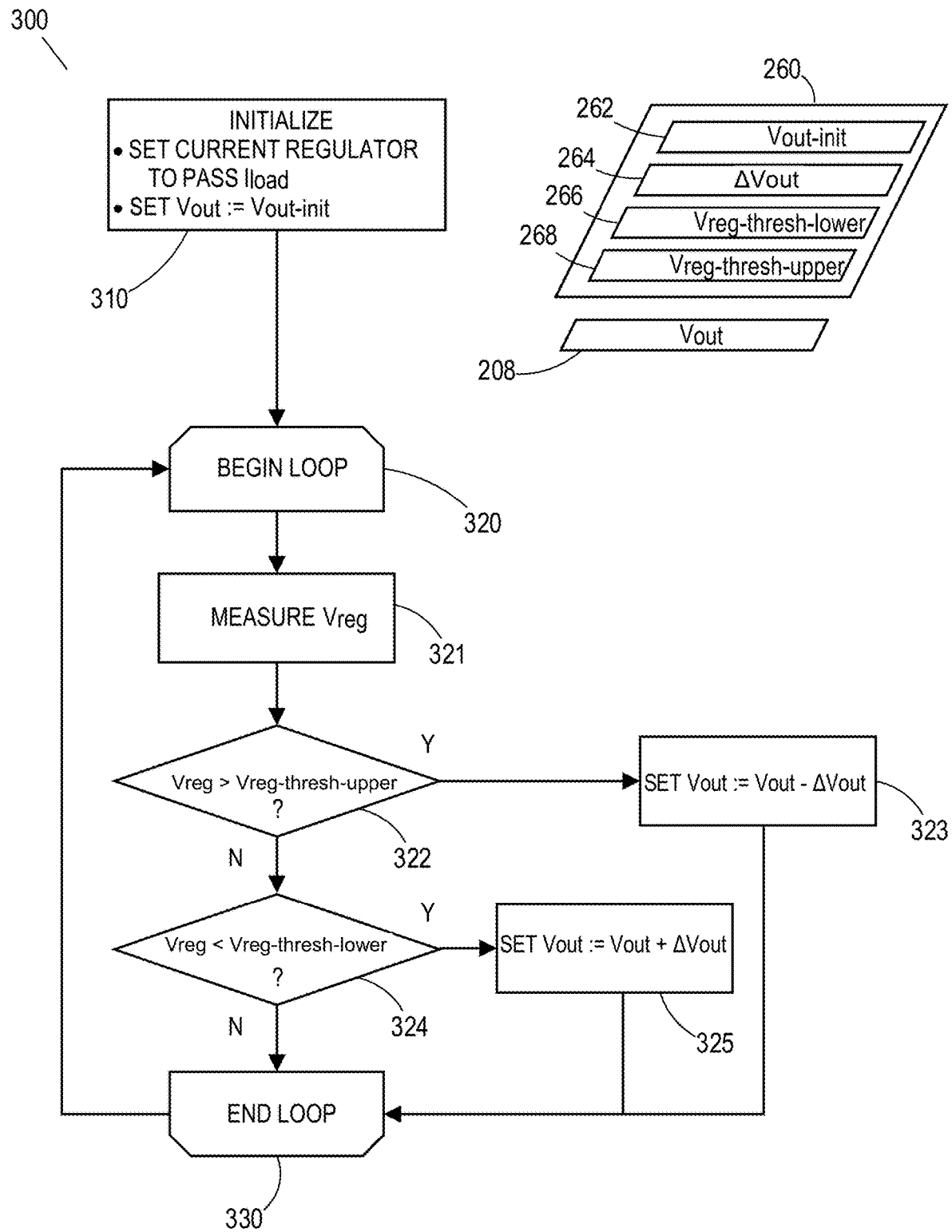
FIG. 3 is a flowchart of a method for providing a regulated current device according to another disclosed aspect.

FIG. 3 is a flowchart of a method 300 for providing a regulated current according to a disclosed aspect. In a related aspect, method 300 is performed by controller 225 of regulated current source device 200a (FIG. 2a).

In an initialization step 310, a current regulator (e.g., current regulator 220 of FIG. 2a) is set to pass a desired external load current Iload, and a voltage booster (e.g., voltage booster 210 of FIG. 2a) is set to output voltage Vout 208 at voltage Vout-init 262. Then, after a regulation loop beginning point 320, a voltage drop $V_{reg}$ across the current regulator is measured in a step 321. At a decision point 322 the measured value of $V_{reg}$ is compared with $V_{reg\text{-}thresh\text{-}upper}$ 268, and if $V_{reg}$ is greater than $V_{reg\text{-}thresh\text{-}upper}$ 268, then in a step 323 voltage $V_{out}$ 208 is set to $V_{out}$-$\Delta V_{out}$.

If, on the other hand, Vreg is not greater than Vreg-thresh-upper 268, then the method continues with a decision point 324, where the measured value of Vreg is compared with Vreg-thresh-lower 266. If Vreg is lower than Vreg-thresh-lower 268, then in a step 325 voltage Vout 208 is set to Vout+ΔVout.

If Vreg is neither higher than Vreg-thresh-upper nor lower than Vreg-thresh-lower, no change is made to Vout, and the loop continues to monitor Vreg. After decision point 322 and/or decision point 324 have been passed, at a regulation loop end point 330, control passes back to regulation loop beginning point 320 and execution continues.

Applications

Application of regulated currents, such as those provided by disclosed regulated current source devices, may be particularly useful in medical and biological applications in a wide variety of treatment scenarios. Specific treatment areas include, but are not limited to:

Musculoskeletal, skin, and soft tissue issues:
spinal pain, both acute and subacute, including discogenic, myofascial, ligamentous, or facet joint pain;
pelvic pain;
thoracic outlet syndrome;
extremity joint pain, acute and/or chronic;
osteoarthritis, rheumatoid arthritis, bursitis;
gout, acute and/or chronic;
trigger point pain;
injuries, acute and/or chronic, including soft-tissue injuries;
post-exercise muscle soreness;
fracture with new pain or chronic pain;
myofascial pain, including joint degeneration and/or spine/disc issues;
skin wound healing, allergy reaction;
workout recovery, calming, or performance;
lymphedema;
sarcopenia;
dermatologic subdermal fat and/or wrinkle reduction;
electro-acupuncture;
Neurological: brain and central nervous system issues:
trigeminal neuralgia;
radiculopathy;
neuroma;
fibromyalgia;
thalamic pain;
shingles: reduction of lesion pain;
PTSD (Post Traumatic Stress Disorder) amelioration;
post-herpetic neuralgia;
peripheral neuropathy;
brain injury with concussion and/or brain fog;
subacute injury of pituitary, hindbrain, midbrain, or medulla;
depression;
relaxation and/or sleep issues;
carpal tunnel syndrome;
Parkinson's disease;
opioid addiction: prevention and withdrawal symptom reduction;
Internal organ issues:
liver issues regarding: toxicity, hepatidides (Inflammation of the liver), fibrosis;
pancreas support and insulin resistance;
GI issues involving: stomach, esophagus, gall bladder, small/large intestines, including constipation;
kidney support, including kidney stone issues;
lung support, bronchitis;
ureteral adhesion;
adrenal support;
uterine bleeding, fibroid issues;
cold/sinus;
general inflammation.

Those skilled in the art to which this Disclosure relates will appreciate that many variations of disclosed aspects are possible within the scope of the claimed invention, and further additions, deletions, substitutions, and modifications may be made to the above-described aspects without departing from the scope of this Disclosure.

The invention claimed is:

1. A regulated current source device for providing a regulated current to a resistive load, the regulated current source device comprising:
a primary electrical energy source for providing an input voltage;
a current regulator, said current regulator being configured and operable to:
pass a predetermined regulated load current by automatically changing its internal resistance, resulting in a varying regulator voltage drop across the current regulator;
a controller, said controller being configured and operable to:
measure the varying regulator voltage drop across the current regulator; and
output a control signal to a control point for controlling a voltage booster via the control point; and
the voltage booster, comprising a power-out point and an input point, said power-out point is connected to a first lead of the resistive load and wherein another output terminal of the regulated current source device is connected to a second lead of the resistive load, wherein said resistive load has a varying resistance, wherein said voltage booster is configured and operable to:
receive at said input point the input voltage;
receive at said control point the control signal; and
adjust output voltage at said power-out point, wherein the adjustable output voltage is controllable via the control signal at the control point of the voltage booster,
according to the measured varying regulator voltage drop, providing the regulated current to the resistive load.

2. The regulated current source device of claim 1, wherein the controller adjusts the output voltage according to a parameter set.

3. The regulated current source device of claim 2, wherein said parameter set comprising:
an initial output voltage value;
an incremental output voltage change value;
a first regulator voltage drop threshold; and
a second regulator voltage drop threshold.

4. The regulated current source device of claim 3, wherein the incremental output voltage change value equals the initial output voltage value.

5. The regulated current source device of claim 4, further comprising a capacitor in a connection between the power-out point of the voltage booster and a local ground.

6. The regulated current source device of claim 5, further comprising a diode in the connection from the power-out point of the voltage booster and the capacitor.

7. The regulated current source device of claim 4, wherein the voltage booster further comprises a shutdown point, which, when signaled with a shutdown signal, causes the voltage booster to cease operation and to provide zero volts output.

8. The regulated current source device of claim 7, further comprising a capacitor in a connection between the power-out point of the voltage booster and a local ground.

9. The regulated current source device of claim 8, further comprising a diode in the connection from the power-out point of the voltage booster and the capacitor.

10. A method for providing a regulated current to a resistive load, the method comprising:
initializing a current regulator to pass a predetermined regulated load current through the resistive load by automatically changing its internal resistance resulting in a varying regulator voltage drop across the current regulator;
initializing a voltage booster to output an initial output voltage to the resistive load, wherein the voltage booster receives an input voltage from a primary electrical energy source, wherein an output voltage of the voltage booster is controllable according to a control signal, and wherein the initializing comprises sending a first control signal to the voltage booster;
measuring the voltage drop across the current regulator to obtain a current regulator voltage drop measure;
comparing the current regulator voltage drop measure to a predetermined upper threshold; and
when the current regulator voltage drop measure is greater than the upper threshold, sending a second control signal to the voltage booster to output a reduced output voltage to the resistive load, wherein the reduced output voltage equals the output voltage minus an incremental output voltage change value;
comparing the current regulator voltage drop measure to a predetermined lower threshold, and
when the current regulator voltage drop measure is less than the lower threshold, sending a third control signal to the voltage booster to output an increased output voltage, wherein the increased output voltage equals the output voltage plus the incremental output voltage change value.

11. The method of claim 10, wherein the incremental output voltage change value equals the initial output voltage.

12. The method of claim 11, wherein the second control signal is a shutdown signal, and wherein the voltage booster ceases operation during a time of the shutdown signal.

13. A regulated current source device for providing the regulated current to the resistive load, the regulated current source comprising:
a primary electrical energy source;
a voltage booster;
a current regulator; and
a controller which is arranged to perform the method of claim 12.

14. The regulated current source device of claim 13, wherein the first regulator voltage drop threshold is less than the second regulator voltage drop threshold.

15. A regulated current source device for providing the regulated current to the resistive load, the regulated current source comprising:
a primary electrical energy source;
a voltage booster;
a current regulator; and
a controller which is arranged to perform the method of claim 11.

16. A regulated current source device for providing the regulated current to the resistive load, the regulated current source device comprising:
a primary electrical energy source;
a voltage booster;
a current regulator; and
a controller which is arranged to perform the method of claim 10.

* * * * *